US012102556B2

(12) United States Patent
Azevedo

(10) Patent No.: US 12,102,556 B2
(45) Date of Patent: Oct. 1, 2024

(54) SYSTEM AND METHOD FOR FALLOPIAN BIRTH CONTROL

(71) Applicant: Max Azevedo, Lenoir, NC (US)

(72) Inventor: Max Azevedo, Lenoir, NC (US)

( * ) Notice: Subject to any disclaimer, the term of this patent is extended or adjusted under 35 U.S.C. 154(b) by 0 days.

(21) Appl. No.: 18/325,626

(22) Filed: May 30, 2023

(65) Prior Publication Data
US 2023/0381012 A1 Nov. 30, 2023

Related U.S. Application Data

(60) Provisional application No. 63/347,402, filed on May 31, 2022.

(51) Int. Cl.
*A61F 6/20* (2006.01)
*A61K 38/48* (2006.01)

(52) U.S. Cl.
CPC ............ *A61F 6/20* (2013.01); *A61K 38/4893* (2013.01); *A61F 2210/0004* (2013.01)

(58) Field of Classification Search
CPC .. A61F 2/97; A61F 2/966; A61F 2/962; A61F 2/95; A61F 2/2436; A61F 6/24; A61F 6/225; A61F 6/22; A61F 6/18; A61F 6/144; A61F 6/142; A61F 6/12; A61F 6/06; A61K 9/0039; A61K 38/4893
See application file for complete search history.

(56) References Cited

U.S. PATENT DOCUMENTS 6,827,931 B1 * 12/2004 Donovan .................. A61P 5/02 424/94.1
7,419,675 B2 9/2008 First
8,071,550 B2 12/2011 Schiffman
8,329,193 B2 12/2012 Gaxiola et al.
11,045,244 B2 6/2021 Zarins et al.
2004/0033241 A1 * 2/2004 Donovan ............. A61K 9/0051 424/239.1
2006/0040894 A1 * 2/2006 Hunter .................... A61P 27/06 514/495
2007/0122466 A1 * 5/2007 Chancellor ............ A61K 9/127 424/450
2016/0015259 A1 * 1/2016 Mody .................. A61B 8/0841 600/106

FOREIGN PATENT DOCUMENTS

WO 2010028770 A1 3/2010

* cited by examiner

*Primary Examiner* — Ophelia A Hawthorne
(74) *Attorney, Agent, or Firm* — Boudwin Intellectual Property Law, LLC; Daniel Boudwin

(57) ABSTRACT

The disclosed invention relates to a system and method for fallopian birth control that utilizes implantable devices that release botulinum toxin or similar acting substances to effectively prevent peristalses of the fallopian tube. The system includes an implantable device, a means for inserting, and an anesthetic. The implantable device is inserted through different methods and is permanent, removable, or degradable so that the process is reversable by recanalization. There is also a corresponding method for utilizing the system and method for fallopian birth control with a tactile device and a visual device.

14 Claims, 3 Drawing Sheets

100 100A

- Implantable Device 110 → Botulinum Toxin 112
- Means for Inserting 120 → Tactile Device 122, Visual Device 124
- Anesthetic 130 → Path of Delivery 132

Applying a Plurality of Botulinum Toxin Interiorly to a Fallopian Tube of a User
310

Applying an Anesthetic Having a Path of Delivery of the Anesthetic to the User
320

FIG. 3

SYSTEM AND METHOD FOR FALLOPIAN BIRTH CONTROL

CROSS REFERENCE TO RELATED APPLICATIONS

This application claims the benefit of U.S. Provisional Application No. 63/347,402, filed on May 31, 2022. The above identified patent application is herein incorporated by reference in its entirety to provide continuity of disclosure.

BACKGROUND OF THE INVENTION

The present invention relates to a system and method for birth control. More specifically, the invention relates to a system and method for fallopian birth control.

Non-surgical means of birth control have been considered through the ages, and recent progress has been directed to substance or material placement into fallopian tubes for permanent sterilization. This recent progress has taken place over the last few decades involving three entities: Bayer, Hologic and Femasys. Bayer has attempted to use a flexible insert, Essure, which is implanted in the fallopian canal consequently creating a permanent occlusion by development of scar tissue in the duct. It thus permanently obstructs passage of sperm or ovum. Hologic, Inc. developed a comparable procedure, Adiana, implanting a grain sized object in the fallopian canal also intended to create an occlusion. Femasys Inc. has a similar approach, but instead of a device it is delivering biocompatible cyanoacrylate adhesive into the fallopian canal. The end goal of this procedure is similar to the Essure and Adiana device in creating an obstruction by tissue ingrowth.

The Bayer device, being of relatively fixed dimensions, is not as susceptible to the contractile and peristaltic motions of the fallopian muscular wall. It is still possible that the device may yield to the fallopian forces and be expelled before tissue ingrowth occurs. The same likely sequence is envisioned with the Adiana procedure. Both the Essure and Adiana procedures have been terminated due to numerous complications.

Femasys has, to date, been unable to commercialize its procedure. The delivery of a bolus of liquid cyanoacrylate monomer into the fallopian canal necessitates rapid polymer formation within the interval of peristaltic activity. The lack of understanding of this phenomenon in attempting to occlude the fallopian canal by these procedures is likely to produce low success.

It is thus contemplated that the formation of a tubal obstruction necessitates the abeyance of the peristaltic muscle actions. Then anesthesia becomes a requirement to keep the bolus of cyanoacrylate motionless or minimally in motion. This is particularly so during the transition from monomer to polymer. Further it is anticipated that all obstructing means or other such formation occur for a moment of time in a relatively peristaltic-free period to form the desired retention to the interior fallopian surfaces. It is of further importance that the fallopian motions be immobilized to permit sufficient time for the liquid to become a solid bolus. There is also an imperative to assure surface contact with the fallopian interior walls for the development of adhesive bonding. It is also anticipated that the formation of adhesive bonding is enhanced by minimizing the fluid environment on the walls of the fallopian tubes.

It is of note that to provide a proper contact surface for bonding to the interior of the duct, provision must be made to minimize the fluids excreted or otherwise coated in this interior. Loose proteinaceous fluids in the fallopian cavity should be minimized by saline flush in order to maximize contact of the delivered substance to the interior and therefore improve adhesive bonding.

As pointed above, there is a need to immobilize peristaltic activity during the performance of the delivery and bonding of the blocking substances. The introduction of a local anesthetic or otherwise immobilizing substance like Botox serves the purpose of preparing the fallopian cavity.

SUMMARY OF THE INVENTION

In view of the foregoing disadvantages inherent in the known types of systems and methods for permanent sterilization now present in the prior art, the present invention provides a system and method that is absent in, and is a prerequisite in procedures of the prior art or any procedure in which one desires to permanently or semi permanently occlude the fallopian ducts.

The fallopian birth control system includes an implantable device, a means for inserting, and an anesthetic.

The fallopian birth control system also includes a corresponding method for tactilely utilizing a fallopian birth control system. The overall method for tactilely utilizing includes the steps of locating a cornual entrance to a fallopian canal of a patient, maneuvering a tactile device to present at one or both cornual entrances to a fallopian channel of the patient, and delivering chemodenervation substance(s) to a fallopian tube of the patient.

The fallopian birth control system also includes a corresponding method for visually utilizing a fallopian birth control system, comprising the steps of applying a plurality of botulinum toxin interiorly to a fallopian tube of a patient, and delivering of an occlusion-creating substance.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 1 shows a system overview of one embodiment of a fallopian birth control system.

FIG. 3 shows a flowchart of one embodiment of a method for visually utilizing a fallopian birth control system.

DETAILED DESCRIPTION OF THE INVENTION

Figure 2:
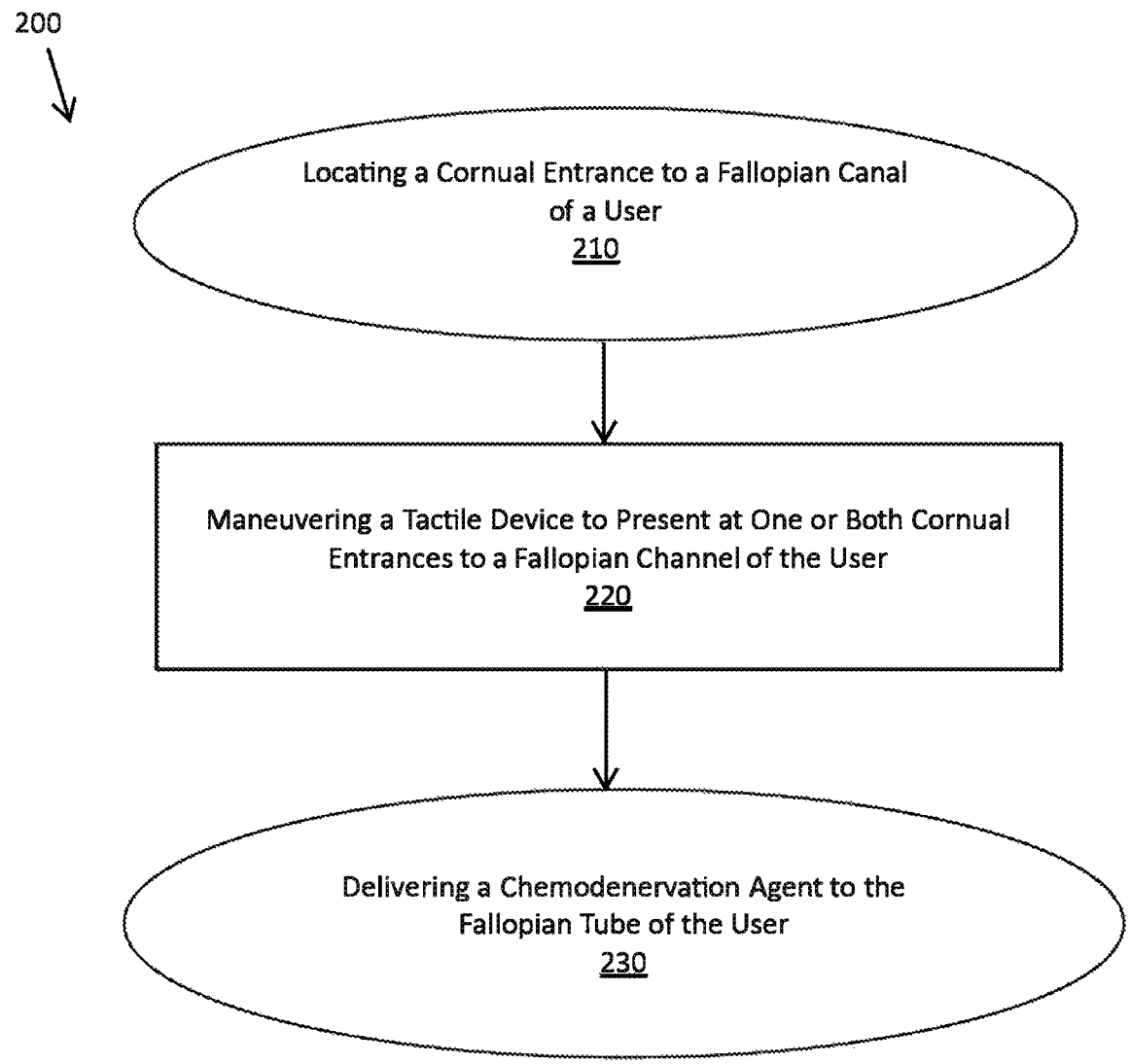
FIG. 2 shows a flowchart of one embodiment of a method for tactilely utilizing a fallopian birth control system.

FIG. 1 shows a system overview of a fallopian birth control system 100. The fallopian birth control system 100 may be a semi-permanent fallopian birth control system 100A or the like. The fallopian birth control system 100 may be a non-surgical system or the like.

The fallopian birth control system 100 may include an implantable device 110, a means for inserting 120, and an anesthetic 130.

The implantable device 110 may be an implantable device 110 that may release a plurality of botulinum toxin 112 or other anesthetizing agent(s) adapted to effectively prevent peristaltic action of a fallopian tube (not shown). The implantable device 110 may be a flexible sliver of porous polymer infused with the botulinum toxin 112 or the like.

More specifically, the implantable device 110 may be adapted to treat a pair of mammalian fallopian ducts resulting in the immobilization of the fallopian canal. The implantable device 110 may be biodegradable or the like and may safely degrade within the pair of mammalian fallopian ducts over an extended period of time.

The means for inserting 120 may be a means for inserting the implantable device. The means for inserting 120 may be a means for inserting a tactile device 122 or the like (See FIG. 2). The means for inserting 120 may be a means for inserting a visual device 124 or the like (See FIG. 3).

The anesthetic 130 may include a path of delivery 132 to deliver the anesthetic 130. The path of delivery 132 may deliver the anesthetic 130 at a cornual entrance from a uterus to a fallopian canal or the like. The path of delivery 132 may deliver the anesthetic 130 through an abdominal wall or the like.

FIG. 2 shows a flowchart for a method for tactilely utilizing a fallopian birth control system 200.

The steps of the overall method 200 may include locating a cornual entrance to a fallopian canal of a user 210, maneuvering a tactile device to present at one or both cornual entrances to a fallopian channel of the user 220, and delivering a chemodenervation agent to the fallopian tube of the user 230.

The locating step 210 may include tactility locating the cornual entrance to the fallopian canal of the user.

The maneuvering step 220 may include the tactile device is a catheter or the like.

The delivering step 230 may include the chemodenervation agent is a plurality of botulinum toxin. The chemodenervation agent may be delivered to the fallopian tube of the user by injection or the like. The chemodenervation agent may be delivered to the fallopian tube of the user by topical contact. The chemodenervation agent may be delivered to the fallopian tube of the subject by a hysteroscope or the like.

FIG. 3 shows a flowchart for a method for visually utilizing a fallopian birth control system 300.

The steps of the overall method for visually utilizing 300 may include the steps of applying a plurality of botulinum toxin interiorly to a fallopian tube of a user 310 and applying an anesthetic having a path of delivery of the anesthetic to the user 320.

The first applying step 310 may include inserting a biodegradable substance, inserting a permanent non-degradable substance, or inserting a flexible sliver of porous polymer infused with a plurality of botulinum toxin.

The second applying step 320 may include the path of delivery is at a cornual entrance from a uterus to a fallopian canal or the path of delivery is through an abdominal wall.

The anesthetic may be of a relatively short duration or possibly for a relatively longer period such as with the use of Botox or other similar agents. The path of delivery may take place at the cornual entrance from the uterus to the fallopian canal or it may be through the abdominal wall. Without adherence to a particular method, the objective is to immobilize the muscular activity either via surface contact or direct injection into the canal tissue or similar anesthetic for immobility.

It is additionally contemplated that a semipermanent birth control may be developed by insertion of a flexible sliver of porous polymer or other similar construct infused with Botox or another similar acting substance. The substance may be a biodegradable material or a permanent non-degradable material of such construct that it may be removed for reversal of the procedure.

The main goal of the present invention is to provide methods and substances to treat mammalian fallopian ducts resulting in a permanent or temporary obstruction that blocks the transport of either/or both egg and sperm from coalescence. The method may utilize visual or tactile means to locate the cornual entrance to the fallopian canal. Any suitable instrument for such a task may be utilized. In one example, the visual device is fitted with tubular passages to permit the insertion of a catheter into the internal passageway of the fallopian canal to deliver substances.

In an embodiment of the method that utilizes tactile means to locate the cornual entrance to the fallopian canal, the tactile device is maneuvered to present a catheter at one or both cornual entrances to the fallopian channel.

After locating the cornual entrance to the fallopian canal, a chemodenervation agent is delivered to the fallopian tube for immobilizing the muscular peristalsis of the structure. Different delivery devices for the chemodenervation agent may be utilized. Other delivery devices may include access to the fallopian tubes via abdominal entry instrumentation. The chemodenervation agent is applied by injection, topical contact or similar methods. In one embodiment, the delivery device is a hysteroscope for placement of the chemodenervating agent and occluding treatment to the fallopian structure. Further, the occluding treatment may be performed before, during or after the occluding process.

For the purposes of presenting a brief and clear description of the present invention, the preferred embodiments will be discussed as used for providing a means for achieving permanent fallopian birth control via controlled dosing of Botox or another similar acting substance.

In all embodiments, the present invention relates to a system and method for permanent fallopian birth control. The method includes applying Botox or a similar substance interiorly to the fallopian tube. In some embodiments, this may be accomplished by insertion of a flexible sliver of porous polymer or other similar construct infused with Botox or another similar acting substance. A further variant of pretreatment is the use of an implant that drives the fallopian fluids distal of the cornual entrance towards ampullary and infundibular segments. The objective of this step is to optimize the adhesion of the implantable substance to effectively adhere and promote scar tissue formation, though it is understood that this implant may serve both as a biodegradable and releasing anesthetic as occlusion occurs.

It is therefore submitted that the present invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A fallopian birth control system, comprising:
   an implantable device releasing botulinum toxin configured for implantation in a fallopian tube and is adapted to effectively prevent passage of an egg out of the fallopian tube of a user;
   a means for inserting the implantable device;
   an anesthetic utilized in combination with releasing botulinum toxin adapted to effectively prevent passage of the egg out of the fallopian tube to immobilize muscular activity; and
   a means for flushing the fallopian tube;
   wherein the implantable device is a flexible sliver of porous polymer infused with botulinum toxin;
   wherein the flexible sliver functions to additionally clear the fallopian tube for placement of cyanoacrylate;
   wherein the implantable device is permanently non-degradable and is safely removable to reverse a fallopian birth control system procedure: and wherein the anesthetic is an infusion in the implantable device.

2. The fallopian birth control system, according to claim 1, wherein the anesthetic includes a path configured for delivery at a cornual entrance from a uterus to the fallopian tube of the user.

3. The fallopian birth control system, according to claim 2, wherein the path of delivery is configured to be through an abdominal wall of the user.

4. The fallopian birth control system according to claim 1, wherein the anesthetic precedes the implantable device.

5. The fallopian birth control system, according to claim 1, wherein the means for flushing is to flush the fallopian tube of the user with saline solution to flush proteinaceous fluid from the fallopian tube of the user to improve adhesion to the fallopian tube of the user.

6. The fallopian birth control system, according to claim 1, wherein the means for flushing is to flush the fallopian tube of the user with a plurality of air to flush proteinaceous fluid from the fallopian tube of the user to improve adhesion to the fallopian tube of the user.

7. The fallopian birth control system, according to claim 1, further comprising a semi-permanent fallopian birth control system such that tubal recanalization is performed.

8. A method for tactilely utilizing a fallopian birth control system, as claimed in claim 1 comprising the steps of:
   locating a cornual entrance to a fallopian canal of a patient;
   maneuvering a tactile device to present at one or both cornual entrances to a fallopian channel of the patient; and
   delivering one or more chemodenervation substances to a fallopian tube of the patient.

9. The method according to claim 8, wherein the tactile device is a catheter.

10. The method according to claim 8, wherein the chemodenervation agent is botulinum toxin and/or other anesthetic.

11. The method according to claim 8, wherein the chemodenervation agent is delivered to the fallopian tube of the patient by injection.

12. The method according to claim 8, wherein the chemodenervation agent is delivered to the fallopian tube of the patient by topical contact.

13. The method according to claim 8, wherein the chemodenervation agent is delivered to the fallopian tube of the patient by hysteroscopic means.

14. The method according to claim 8, wherein the chemodenervation agent is delivered to the fallopian tube of the patient by tactile sensing of the cornual entrance.

* * * * *